United States Patent
Aarts et al.

(10) Patent No.: US 12,310,795 B2
(45) Date of Patent: May 27, 2025

(54) ULTRASOUND CONTROLLER UNIT AND METHOD

(71) Applicant: KONINKLIJKE PHILIPS N.V., Eindhoven (NL)

(72) Inventors: Ronaldus Maria Aarts, Geldrop (NL); Franciscus Hendrikus van Heesch, Valkenswaard (NL); Rick Bezemer, Utrecht (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 802 days.

(21) Appl. No.: 17/262,857

(22) PCT Filed: Jul. 16, 2019

(86) PCT No.: PCT/EP2019/069057
§ 371 (c)(1),
(2) Date: Jan. 25, 2021

(87) PCT Pub. No.: WO2020/020692
PCT Pub. Date: Jan. 30, 2020

(65) Prior Publication Data
US 2021/0315546 A1  Oct. 14, 2021

(30) Foreign Application Priority Data
Jul. 24, 2018  (EP) .................................... 18185249

(51) Int. Cl.
*A61B 8/00* (2006.01)
*G16H 40/40* (2018.01)
(Continued)

(52) U.S. Cl.
CPC .......... *A61B 8/5269* (2013.01); *A61B 8/4236* (2013.01); *A61B 8/4488* (2013.01);
(Continued)

(58) Field of Classification Search
None
See application file for complete search history.

(56) References Cited

U.S. PATENT DOCUMENTS 9,320,498 B2  4/2016  Seo et al.
9,668,714 B2  6/2017  Call et al.
(Continued)

FOREIGN PATENT DOCUMENTS

| CN | 104739449 A | | 7/2015 |
|---|---|---|---|
| WO | WO 2014/021105 | * | 2/2014 |
| WO | WO 2018/109490 | * | 6/2018 |

OTHER PUBLICATIONS

English Translation of WO 2014/021105 (Year: 2014).*
(Continued)

*Primary Examiner* — Katherine L Fernandez

(57) ABSTRACT

An ultrasound controller unit (22) for controlling an ultrasound transducer unit (24) in acquiring ultrasound data for the purpose of deriving one or more physiological parameter measurements. The controller is adapted to control weighting coefficients applied to transmit and receive signals of each of a plurality of transducer elements (26) of the transducer unit. The controller is adapted to detect any artifact in received data affecting (e.g. obscuring) the output path of one or more of the transducers, and to identify the affected transducer elements. The weighting coefficients of the non-affected transducer elements are then adjusted so as to minimize an estimated noise component in the parameter measurement, if derived using only the non-affected transducer elements. Measurements of the one or more parameters are then derived by collecting data from the non-affected transducers only, these being configured with the optimized weighting coefficients.

17 Claims, 3 Drawing Sheets

(51) Int. Cl.
G16H 40/63 (2018.01)
G16H 50/30 (2018.01)
G16H 50/70 (2018.01)

(52) U.S. Cl.
CPC .............. *A61B 8/54* (2013.01); *G16H 40/40* (2018.01); *G16H 40/63* (2018.01); *G16H 50/30* (2018.01); *G16H 50/70* (2018.01)

(56) References Cited

U.S. PATENT DOCUMENTS

| | | | |
|---|---|---|---|
| 2006/0058671 A1* | 3/2006 | Vitek | A61N 7/02 600/447 |
| 2011/0077484 A1 | 3/2011 | Van Slyke et al. | |
| 2013/0006108 A1* | 1/2013 | Yoshiara | G01S 15/8927 600/431 |
| 2013/0253325 A1* | 9/2013 | Call | A61B 8/5246 600/447 |
| 2013/0304405 A1 | 11/2013 | Schmid et al. | |
| 2015/0245818 A1* | 9/2015 | Zhai | A61B 8/488 600/453 |
| 2016/0354062 A1 | 12/2016 | Hwang | |

OTHER PUBLICATIONS

International Search Report and Written Opinion for International Application No. PCT/EP2019/069057, filed Jul. 16, 2019, 14 pages.
Stankwitz et al., "Nonlinear Apodization for Sidelobe Control in SAR Imagery", IEEE TR. Aerospace and El. S., V.31:1, Jan. 1995, pp. 267-279.
Reeg, J., "Null Subtraction Imaging Technique for Biomedical Ultrasound Imaging", MSc Thesis, University of Illinois at Urbana-Champaign, 2016, 47 pages.

* cited by examiner

ULTRASOUND CONTROLLER UNIT AND METHOD

RELATED APPLICATIONS

This application is the U.S. National Phase application under 35 U.S.C. § 371 of International Application No. PCT/EP2019/069057, filed on Jul. 16, 2019, which claims the benefit and priority to European Application No. 18185249.2, filed Jul. 24, 2018, which is incorporated by referenced in its entirety.

FIELD OF THE INVENTION

The invention relates to an ultrasound controller unit for optimizing ultrasound data collection in the presence of an obstructing artifact.

BACKGROUND OF THE INVENTION

Ultrasound imaging is a widely used imaging modality for visualizing anatomical structures. The imaged structures are usually analyzed and interpreted by an expert. Another use of ultrasound is to monitor parameters of such structures, such as the diameter of a blood vessel or the heart rate.

The typical approach to parameter estimation comprises a first step of reconstructing images from input ultrasound data, followed by a second step of parameter estimation, based on the reconstructed images. Image reconstruction typically entails beam steering, signal compounding of one or more sonifications (ultrasound signal propagations), followed by scan format conversion and image enhancements. The parameter estimation process then uses an output reconstructed image sequence to derive one or more values of the parameter, for instance as a function of time. This parameter estimation can then be used to output an overlay of the image sequence with the parameter.

In certain applications, it may be advantageous or necessary for a system to perform a process of enhancement to dynamically improve the quality or accuracy of the output parameter estimation. This can often be the case for instance where physical set-up of the system is liable to shift or change, leading to deterioration in the accuracy of the parameter estimation.

For example, in operator-free, body-worn ultrasound monitoring applications (for example using a body-mountable patch having an ultrasound transducer array embedded therein), measurements may be acquired over an extended period (for example, hours or days). During this time the acoustic coupling of the ultrasound (on-body) probe to the body (typically skin) can deteriorate. For example, ultrasound gel that is commonly used to facilitate even acoustic coupling can evaporate. Additionally, air bubbles can become trapped in the ultrasound gel layer, and the position of these bubbles may slowly change over time, interfering with the ultrasound signal. In the case of this suboptimal acoustic coupling, ultrasound signals will suffer from interference. This reduces the quality of the reconstructed image as well as the consecutive parameter estimation that uses the reconstructed images as an input.

This problem of suboptimal acoustic coupling is known. The typically adopted approach to address the issue is to introduce steps to enhance or optimize the image reconstruction. By optimizing the image reconstruction step, the parameter estimation is typically also improved. Approaches are typically based on rendering the beamforming and data compounding processes of image reconstruction content-adaptive, often by adjusting parameters of an apodization process applied to the ultrasound probe signal outputs.

Apodization is an optical filtering technique which is based on changing the shape of the ultrasound signal waveform, often to remove Airy disks caused by diffraction around an intensity peak, improving the focus. The sidelobes of the Airy disk are primarily responsible for degrading the image, and so apodization is often based on sidelobe suppression.

Exploiting apodization to improve Synthetic Aperture Radar (SAR) image formation by sidelobe control for example is well known, e.g. from H. C. Stankwitz et al., Nonlinear apodization for Sidelobe Control in SAR Imagery, IEEE TR. Aerospace and El. S., V.31:1, January 1995, pp. 267-279.

In ultrasonic imaging, the reduction of lateral sidelobes results in an improved image with less distortion and fewer artifacts. In general, apodization is used to reduce sidelobes in exchange for increasing the width of the central lobe and thus decreasing lateral resolution.

An improvement on this however is provided by null subtraction imaging (NSI). This is a non-linear image processing technique which applies multiple apodizations to multiple copies of the same image to reduce sidelobe levels while also improving lateral (and temporal) resolution (see e.g. JONATHAN R. REEG, Null subtraction imaging technique for biomedical ultrasound imaging, MSc Thesis, University of Illinois at Urbana-Champaign, 2016).

A further example is described in US20160354062. This proposes a method which comprises segmenting a beam signal into a main lobe component and a sidelobe component, to improve the images.

However, while optimizing the image reconstruction step does typically lead to improvement in parameter estimation, this approach is neither optimal for improving the accuracy of the output parameter estimation, nor efficient in terms of processing steps.

To demonstrate this, an example is depicted in FIG. 1. Each of FIGS. 1(a)-(c) show propagation of an ultrasound signal 16 by an ultrasound transducer array 14 into a region of a subject's body. The aim is to estimate an average width of the black rectangular structure indicated at arrow 12 (where there is no vascular obstruction). FIG. 1(a) shows the case in which there is ideal acoustic coupling between the transducer array and the body surface. The ultrasound signal is able to extend across the whole of the obstruction being measured.

FIG. 1(b) however shows the case in which there is only partial acoustic coupling between the transducer array and the skin surface. A middle portion of the array has become de-coupled for instance due to presence of an artifact such as an air bubble between the contact surfaces or a non-smooth surface area. As a result, a part of the window under the ultrasound array is not reconstructed correctly (only the parts inside the white outlines will be correctly reconstructed).

FIG. 1(c) illustrates the typical approach to addressing the partial de-coupling, which is based on adapting the transmit beam shape (as shown) and adapting the receive-apodization. From this, an optimal picture (showing the vascular occlusion 12) is reconstructed (image reconstruction optimized).

However, while the solution shown in FIG. 1(c) improves the coverage of ultrasound image, leading to improved image reconstruction, the total signal-to-noise ratio will be reduced compared to FIG. 1(b) in the non-occluded areas. As a result, the quality of parameter estimation is not as high as it might otherwise be.

An improved approach to addressing the issue of imperfect acoustic coupling in the case of physiological parameter estimation is generally required.

U.S. Pat. No. 9,668,714B2 discloses an ultrasound arrangement for determining physiological parameters in the presence of a physical blockage obscuring part of the ultrasound aperture. The disclosure proposes setting weighting coefficients during an ultrasound image recontruction to individual transmit apertures of the transducer based upon a degree of blockage of the aperture when using circular driving waves. For example, for fully blocked apertures, a weighting of zero is applied, for non-affected apertures, a weighting of one, and for partially blocked, the weighting is between zero and one in proportion to the degree of blockage.

SUMMARY OF THE INVENTION

The invention is defined by the claims.

According to examples in accordance with an aspect of the invention, there is provided an ultrasound controller unit for receiving and processing ultrasound data to derive a measure of at least one physiological parameter, the unit being operably coupleable with an ultrasound transducer unit, for controlling the transducer unit to acquire the ultrasound data, and for controlling a set of amplification weighting coefficients applied to transmitted and received ultrasound signals of each of a plurality of transducer elements of the transducer unit, including at least one weighting coefficient for each transducer element, the ultrasound controller unit being adapted to:

receive ultrasound data from the transducer unit, perform artefact detection to detect the presence of any artefacts in the received data, and associate any detected artefacts with one or more of the transducer elements, perform an optimization procedure for the at least one physiological parameter measurement, comprising adjusting the weighting coefficients of the non-associated transducer elements to minimize an expected noise component in the derived physiological parameter measurement when derived from data of the non-associated transducers only, and acquire further ultrasound data using only the non-affected transducer elements, the elements being configured with the optimized weighting coefficients, and derive measures of the at least one physiological parameter based on said further acquired data.

Preferably the further measurements are derived directly from the ultrasound data without the need for image reconstruction. For example, parameter measurements may be based on a model permitting raw ultrasound data signals to be transformed into parameter measurements, or permitting the measurements to be inferred from the data.

The invention is based on identifying which of the transducer elements is affected or obstructed by the artifact and adjusting the weighting coefficients of the non-affected transducer elements, so as to optimize signal quality of the_physiological parameter being measured. The affected transducer elements are discounted or deactivated for further measurements.

The invention hence differs from the prior art in that weighting coefficients of non-affected transducer elements are adjusted and that they are adjusted to optimize the physiological parameter being measured.

The invention is based on the key technical insight that discounting data from a portion of the transducer elements (the obstructed elements) will have an effect on the degree of error (noise) in the measured parameter, even though the signal quality of the collected raw data of the remaining transducer elements has not changed. This is because the physiological parameter is a product of the ensemble of data of the whole array of transducer elements.

It is also based on the insight that adjusting the weightings of the remaining non-affected transducer elements can alter the degree of noise in the obtained parameter. This is often for instance due to geometrical considerations. For instance, output paths and angles of some transducer elements, for instance those with a certain optimal alignment with or at a certain proximity to the anatomical object to which a measured parameter pertains, will be better suited to obtaining high quality measurements of the parameter from their signal data.

Hence, a significant technical improvement can be obtained by implementing an optimization step, based on optimizing signal-to-noise of the physiological parameter under measurement, through adjusting weighting coefficients of transducer elements.

The weighting coefficients are amplification weighting coefficients. The set of weighting coefficients includes at least one (individually configurable) weighting coefficient for each transducer element. In some examples, each transducer element may have an independently controllable amplification coefficient for both transmitted signals and received signals. In this case, the transducer element may be configurable with at least two amplification weighting coefficients.

The level of an amplification weighting coefficient for a given transducer element will at least partly determine the strength of the contribution made by the element to the overall ultrasound data and ultimately the derived physiological parameter. Hence, lowering the weighting coefficient(s) for a given transducer element will reduce its contribution. The aim of preferred embodiments of the present invention is to set relative lower weightings to transducer elements the data for which contributes relatively highly to the noise component of the overall physiological parameter measure (and vice versa).

The controller is coupleable with a transducer unit for controlling the transducer unit and controlling the set of weighting coefficients. For example, the controller may be coupleable with a transducer unit and operable to output a coupled transducer unit the set of weighting coefficients. The controller may be operable to output one or more control commands for controlling acquisition of ultrasound data.

An artifact, referred to above, may mean an obstruction or blockage or occlusion in the field of view of the transducer unit, for instance caused by separation in the coupling between the transducer unit and the body. It may include by way of example air bubbles in an interfacing medium between the transducer unit and the body and/or one or more bone-structures.

Associating the artifact with one or more of the transducer elements may mean identifying transducer element(s) whose transmitted or received signals are affected by the artefact or most affected by the artifact (e.g. intercepted by the (cause of) the artefact or most prominently intercepted by it).

It may mean identifying the transducer elements whose contributions to the measurement are too low, due to (partially or fully) blocked or obstructed signal paths by the artefact.

It may mean identifying the transducer elements whose signal output and/or input paths (or areas) intercept or encompass the artefact or the structural cause of the artefact, or have it most centrally within their output path or area.

It may mean identifying which of the transducer elements is spatially aligned with the artifact.

Minimizing the expected noise component can be performed with different approaches, and which approach is appropriate will depend upon the parameter being measured.

One approach is based on optimizing signal quality at the level of individual ultrasound transducers. In this case, the expected noise component is based on detected signal noise in ultrasound signals received at the transducer elements in the presence of the artifact.

For example, according to at least one set of embodiments, the optimization procedure may comprise applying relative higher amplitude weightings to transducer elements for which received ultrasound signals at the element in the presence of the artefact exhibit a higher signal to noise ratio, and applying relative higher weightings to transducer elements for which received ultrasound signals exhibit relative higher noise.

In a similar, related approach, the expected noise component for each ultrasound transducer element may be based on a determined deviation of received ultrasound signals at the transducer element in the presence of the artifact from an average of received ultrasound signals across all or a subset of all of the transducer elements of the transducer unit. Higher deviating elements may be assigned lower weighting coefficients and vice versa. Hence, here effectively a noise component in signals of each transducer element is estimated based on a deviation in the ultrasound signal data from an average taken across the whole set, or part of the whole set, of ultrasound elements. Hence a variance of the ultrasound signals across the set of transducer elements is minimized.

In both cases, the approach is based on the insight that upon discounting data from a section of the transducer elements, sensitivity of the measured parameter to noise in the raw data collected by each transducer element is increased. Hence a significant technical benefit can be obtained by simply adjusting the weighting coefficients to give relatively less weight to transducer elements whose signal data is relatively noisier in the presence of the artefact and relatively more weight to those whose data is relatively less noisy.

The optimization procedure is hence in this case based on minimizing noise in the source signals.

In a further approach, the optimization procedure may be based on use of an estimation procedure to estimate expected values of the at least one physiological parameter and/or the expected noise component of the physiological parameter when derived using data of different subsets of one or more of the transducer elements. For example, there may be estimated values of the noise component contributed to a derived physiological parameter by each of the non-affected transducer elements individually, or to subsets of these.

Weighting coefficients are then assigned to the transducer elements in dependence upon said expected values.

Higher weighting coefficients maybe applied to those transducer elements for which lower error is estimated in the physiological parameter derived from those elements.

The estimation procedure may for example be based on a model or theoretical equation for deriving the parameter and/or the error based on received data.

In an alternative set of examples, the optimization procedure may be based on use of an estimation procedure to estimate expected values of the at least one physiological parameter and/or expected noise component of the physiological parameter if derived from the non-associated transducer elements being configured with different sets of possible weightings. In other words, the expected noise component is derived based on use of this estimation procedure.

This may estimate expected parameter values or an estimated error component if derived either from the full set of non-affected transducer elements or from one or more subsets, the elements configured in either case with a particular set of weighting coefficients.

This approach arrives more directly at an optimized set of weightings by considering directly the effect of different weightings. It may be based on calculating expected derived parameter values for data of each element with each of one or more weightings and combining, or may be based on a combined model or equation or algorithm capable of determining overall parameter or noise values with different ensembles of weightings.

The estimation procedure may in certain examples be based on a determined or pre-determined relative position of an anatomical element to which the physiological parameter to be measured pertains, relative to the ultrasound transducer unit. An anatomical element may for instance be a particular anatomical body such as a blood vessel or an organ. It may be an anatomical region, for instance encompassing a whole anatomical body such as a blood vessel or an organ or a part of one, such as a section of a blood vessel or one ventricle or ventricular region of the heart for instance.

The position of a transducer element relative to the anatomical element to which a measured parameter pertains may affect the quality of the parameter measurement derivable from ultrasound data acquired using this element. This is particularly so in the case that physiological parameters are to be determined without generating an ultrasound image (i.e. based directly on the obtained ultrasound data, e.g. upon patterns in the data).

For example, some ultrasound elements will naturally be better aligned in terms of their (plane wave) output paths with the anatomical element or region of interest. Hence, data acquired from these elements will be better for deriving measures of a physiological parameter pertaining to that anatomical element.

Hence in some examples, estimated noise component of a transducer element may be estimated as being in proportion to or in dependence on a degree of alignment of a transducer element to the anatomical element of interest.

Additionally or alternatively, estimated noise component of a transducer element may be estimated as being in proportion to or in dependence on a proximity e.g. a distance of a transducer element to the anatomical element of interest.

In examples, the relative position of said anatomical element may be determined based on analysis of patterns in the further ultrasound data, without generation of an ultrasound image.

This may be based for example on use of an anatomical model of the element as represented in terms of one or more characteristic patterns detectable in the ultrasound data, for instance these representing different structural parts or portions of the anatomical element. A pattern may for instance comprise a series of different frequency wave parts, e.g.

higher frequency, lower frequency, higher frequency. From the delay between sections of the characteristic pattern, size of each of the structural parts may be determined.

The estimation procedure may be based on use of a stored dataset of prior data relating to previously derived values of the physiological parameter.

The prior data may include prior derived parameter measurements for different sets of applied weightings and/or for data of different subsets of one or more transducer elements. The prior data may include or indicate prior trends or patterns in the parameter values over a time series, in examples.

The data can be used for different purposes. The prior data can be used as a basis for deriving the estimated parameter values or noise components for different subsets of one or more transducer elements. For example, an average past value can be derived for a particular element or subset based on prior values, and used to inform an estimated value of the parameter.

Additionally or alternatively, the data can be used to derive an estimate of a noise component in the data based on independently deriving estimated values of the parameter, and comparing these with past data or trends in the data.

Accordingly, the estimation procedure may be based on comparing derived estimated values of the at least one parameter using different sets of weightings or using different subsets of one or more transducer elements with prior data in said stored dataset, to thereby derive an estimation of a noise component of said values, based on identified disparities.

The deriving the physiological parameter measurements using the optimized weighting coefficients may comprise directing one or more ultrasound plane waves toward an anatomical element to which the physiological parameter pertains. This leads to greater signal to noise ratio of measured physiological parameters, for reasons that will be explained below with reference to FIG. 2.

The deriving the physiological parameter measurements using the optimized weighting coefficients may be based on analysis of the ultrasound data without generating an ultrasound image. This approach to measuring parameters is known in some other, unrelated, technical fields, for instance for finding cracks in concrete, or the level of inflation in vehicle tires (see for instance US 2015/061852 A1). It is not known in the field of physiological parameter measurement. This approach may in general yield higher signal to noise ratio for reasons that will be explained below with reference to FIG. 2.

According to any embodiments, the deriving of the further measurements may comprise compounding data acquired from each of one or more consecutive sets of the non-associated transducer elements.

Optionally, the compounding may comprise averaging, e.g. a weighted average. The consecutive sets refers for example to each uninterrupted chain or block of elements, e.g. on either side of the artifact or obstruction.

The artefact detection may according to any embodiment comprise monitoring received ultrasound data and/or measurements for a characteristic deviation in the data or measurements from previously acquired measurements. The characteristic deviation may mean a deviation of a threshold size or magnitude, or a deviation having a particular shape or pattern in the associated waveform. The deviation may mean a change in the parameter exhibiting a particular gradient or steepness (in time).

A further aspect of the invention provides a body-mountable ultrasound unit comprising:

an ultrasound transducer unit comprising a plurality of transducer elements and having a set of configurable amplification weighting coefficients for applying to transmitted and received ultrasound signals the transducer elements, including at least one configurable weighting coefficient for each transducer element; and an ultrasound controller unit as described in any example or embodiment detailed above or below, or as claimed in any of claim of this application, operably coupled with the transducer unit for controlling the transducer unit.

The transducer unit may take any form. It may in some examples be a self-contained (e.g. encapsulated or housed), discrete unit or may consist simply of an arrangement or assembly of transducer elements, comprised by the body-mountable ultrasound unit, e.g. integrated or housed in the unit.

The body mountable ultrasound unit may be releasably coupleable to a surface of the body (e.g. skin, for example having means for adhering to a surface of the body, e.g. via a layer of adhesive. The body-mountable unit may be arranged for releasably mounting to or around a part of the body, for example, mountable to the wrist, neck, chest, leg or ear.

A body-mountable unit allows for extended periods of monitoring, for example at a patient's home, or otherwise away from a clinical environment.

In particular examples, the body-mountable unit may be in the form of a body-mountable patch. The patch may for instance comprise a layer of adhesive for adhering the patch to the skin of the patient.

A further aspect of the invention provides a method of configuring an ultrasound transducer unit, the transducer unit being adapted to acquire ultrasound data for deriving a measure of one or more physiological parameters, and having a configurable set of amplification weighting coefficients applied to transmitted and received ultrasound signals of a plurality of transducer elements of the transducer unit, including at least one weighting coefficient for each transducer element, the method comprising:

receiving ultrasound data from the transducer unit; performing artefact detection to detect the presence of any artefacts in the received data, and associating any detected artefacts with the signal data of one or more of the transducer elements;

performing an optimization procedure for the at least one physiological parameter measurement, comprising adjusting the amplification weighting coefficients of the non-associated transducer elements to minimize an expected noise component in the physiological parameter measurement when derived from data of the non-associated transducer elements only, and acquiring further ultrasound data using only the non-affected transducer elements, the transducer elements being configured with the optimized weighting coefficients, and deriving further measurements of the at least one physiological parameter based on said further acquired data.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
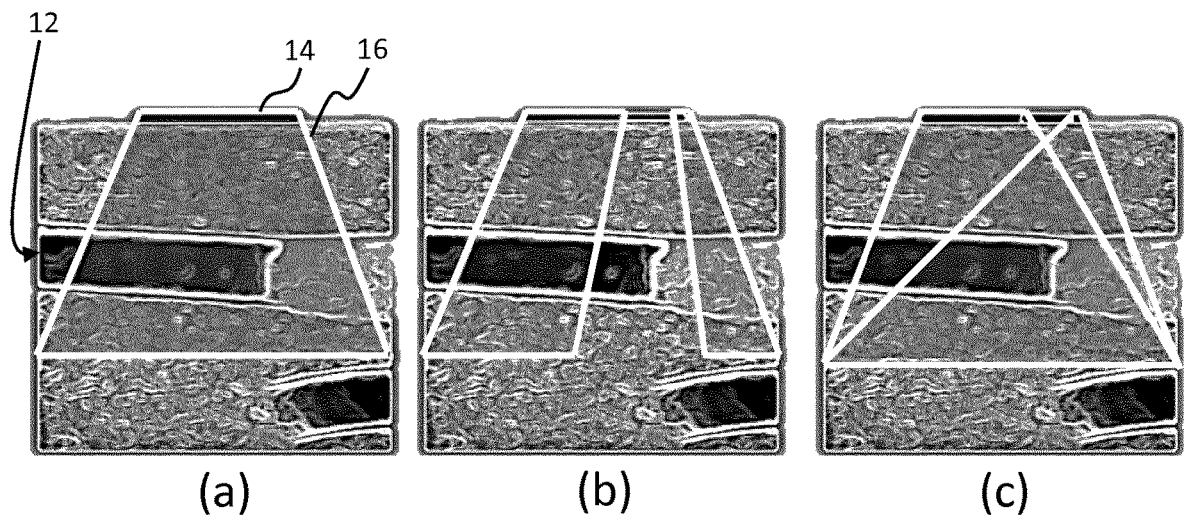
FIG. 1 illustrates a known approach to addressing transducer de-coupling based on beam-steering and optimizing image reconstruction.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an ultrasound controller unit for controlling an ultrasound probe in acquiring ultrasound data for the purpose of deriving one or more physiological parameter measurements. The controller is adapted to control weighting coefficients applied to transmit and receive signals of each of a plurality of transducer elements of the transducer unit. The controller is adapted to detect any artifact in received data affecting (e.g. obscuring) the output path of one or more of the transducers, and to identify the affected transducer elements. The weighting coefficients of the non-affected transducer elements are then adjusted so as to minimize an estimated noise component in the parameter measurement, if derived using only the non-affected transducer elements. Measurements of the one or more parameters are then derived by collecting data from the non-affected transducers only, these being configured with the optimized weighting coefficients. Preferably, parameter measurements are derived without performing image reconstruction, based on the ultrasound data alone.

Adjusting the weightings to minimize an estimated noise component may be approached in at least two different ways. One approach is based on minimizing noise at the level of individual transducer signals, for example by reducing weightings for transducers whose returned signals in the presence of the artefact exhibit a high noise component or low SNR. Another approach is to minimize noise at the (higher) level of the measured parameter itself, for example by using a model or estimation algorithm for estimating the parameter and/or the error component, this being based on prior derived or observed patterns in the data, allowing estimation of the expected parameter or noise when different weightings are used.

Figure 2:
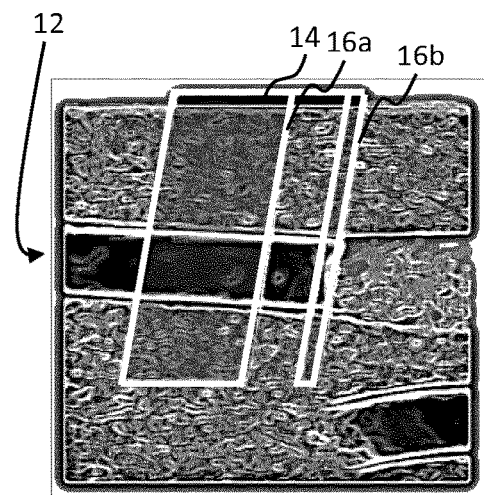
FIG. 2 illustrates an example approach according to the invention, based on propagating a planar wave.

FIG. 2 schematically illustrates one simple example for instance. This is presented by way of contrast to the prior art approach illustrated in FIG. 1, discussed above. In contrast to the approach of FIG. 1, for optimal parameter estimation, a planar wavefront directly sent towards the object of interest (the region of interest 12 in this case) would yield a better result. This is shown in FIG. 2. Here, a simple planar wavefront 16a, 16b is sent from each consecutive set of non-affected transducer elements of the transducer array 14 toward the region of interest 12.

The resulting wavefront is more efficient in terms of computing power required for its generation and processing, and yields a higher contrast compared to the steered wavefront of FIG. 1(c) because of its higher density. This is because, for the purposes of parameter estimation, the received signal could be simply averaged over the receiving transducer elements, instead of calculating pulse delays based on the beam angles as shown in FIG. 1(c).

As a result, despite the fact that only a partial image could be reconstructed from the data, a higher signal to noise is obtained in the physiological parameter under measurement, and with less processing power. This output projection can be arrived at by adjusting the amplification weighting coefficients applied to both transmit and receive signals of each of the non-affected transducer elements and setting a constant or linear transmit and receive (pulse) delay for the transducer elements.

The weighting coefficients of the transducer elements may be adjusted according to the quality of parameter estimation expected to be derivable from their data, i.e. the contribution each is expected to make to the signal-to-noise of the derived parameter measurement. This may be based on an estimated noise component contributed to a physiological parameter measurement by data of each of the transducer elements.

This may in part for instance derive from geometrical factors. For example, in a three-dimensional transducer array transmitting a plane wave toward a vessel, some transducer elements will have output paths which more directly or accurately intercept or bisect the vessel, and measurements obtained from the data of these elements will naturally be of higher quality and contribute to high signal to noise in the parameter measurement. Ideally these should be assigned a higher amplification weighting. By contrast transducer elements poorly aligned with the anatomical element to which the measured parameter pertains will generate noise in the derived parameter measurement. Ideally, these should be assigned a lower amplification weighting.

Optimizing the weighting coefficients is based on selecting weighting coefficients so that noise in the derived parameter may be minimized. In one set of examples, this may be derived experimentally, for instance by transmitting signals from each transducer element, deriving a measurement of the parameter of interest from its data, and determining a signal-to-noise level of the measurement (i.e. a quality of the measurements). Weightings may be set in dependence upon these levels. Alternatively, this may be derived analytically, based on a model, for example based on a geometrical model or shape and/or position of the anatomical element/body to which the measured parameter pertains, for instance its position in relation to the set of transducer elements of the transducer unit. From this, an estimated signal-to-noise contribution of the data derived from each transducer element may be derived, based for instance upon the respective transducer element's position (e.g. angular position and/or distance) relative to the anatomical element to which the measured parameter pertains.

Embodiments of the invention provide an ultrasound controller unit for receiving and processing ultrasound data to derive at least one physiological parameter measurement.

The controller unit is operably coupleable with an ultrasound transducer unit, for controlling the transducer unit to acquire the ultrasound signal data.

Figure 3:
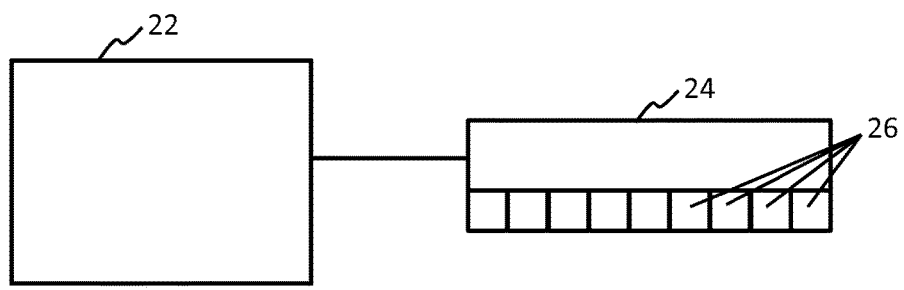
FIG. 3 is a block diagram showing components of an example controller unit according to the invention, shown operably coupled to a transducer unit.

FIG. 3 shows an example system comprising a controller unit 22 according to one or more embodiments of the invention, the controller unit shown operably coupled to an example ultrasound transducer unit 24. The controller may be provided alone, adapted for coupling to an ultrasound transduce unit, e.g. a probe. The controller may comprise a connection interface for facilitating the coupling. Alternatively, a system may be provided comprising both a controller unit and a coupled ultrasound transducer unit.

The ultrasound transducer unit 24 comprises a plurality of ultrasound transducer elements 26. These are provided as an array of transducer elements in the example of FIG. 3. The controller unit 22 is operable to control a set of amplification weighting coefficients applied to transmitted and received ultrasound signals of each of the transducer elements of the transducer unit.

The controller unit 22 is adapted to receive ultrasound data from the transducer unit 24 for measuring the one or more physiological parameters. The controller is further adapted to perform artefact detection to detect the presence of any artefacts in the received data, and to subsequently associate any detected artefacts with the signal data of one or more of the transducer elements 24.

The controller unit 22 then performs an optimization procedure for the at least one physiological parameter measurement, which comprises adjusting the amplification weighting coefficients of the non-associated transducer elements 24 to minimize an expected noise component in the physiological parameter measurement when derived from data of the non-associated transducers only.

The amplification weighting coefficients are implemented as signal amplifiers for each element. They define a gain of the respective transducer element. The coefficients applied to the transmitted signal define a transmit gain, and the coefficients applied to the received signals define a receive gain.

Typically, it is possible to separately define a transmit gain and a transmit pulse delay. These together define beam shape. Adjusting them can also be used to adjust a shape of the ultrasound signal waveform, for instance to remove Airy disks (side-lobes) caused by diffraction around an intensity peak, improving the focus.

Following this, the controller unit 22 is adapted to acquire further ultrasound data using only the non-affected transducer elements 24, the elements being configured with the optimized weighting coefficients, and derive further measurements of the at least one physiological parameter based on the acquired data.

The deriving the physiological parameter measurements using the optimized weighting coefficients may in some example comprise directing one or more ultrasound plane waves toward an anatomical element to which the physiological parameter pertains (for instance a blood vessel). This leads to greater signal to noise ratio of measured physiological parameters, for reasons explained above with reference to FIG. 2.

The deriving the physiological parameter measurements using the optimized weighting coefficients may be based on analysis of the ultrasound data performed without generating an ultrasound image. As noted above, this approach to measuring parameters is known in some other, unrelated, technical fields, for instance for finding cracks in concrete, or the level of inflation in vehicle tires (see for instance US 2015/061852 A1). It is not known in the field of physiological parameter measurement. This approach may in general yield higher signal to noise ratio for reasons that will be explained below with reference to FIG. 2.

By way of non-limiting example, the one or more physiological parameters for measuring may include the size or dimension of a physiological structure such as a blood vessel, or a chamber (e.g. ventricle) of the heart, or the diameter of a bone. The parameter may include blood flow, heart rate, a pulse rate or pulse volume, a blood oxygen level (e.g. $SpO_2$) or a breathing rate.

The artifact detection may according to some examples comprise monitoring received ultrasound data and/or measurements for a particular deviation characteristic in the data or measurements, corresponding to a certain deviation from previously acquired data or measurements. For example, the controller unit 22 may monitor for a change in the value of a parameter being monitored of a certain threshold size or magnitude. Additionally or alternatively, the controller unit 22 may monitor for change in the parameter value which is of a threshold abruptness (i.e. rate of change with time), e.g. more than 5% change within a 5 second period.

Associating the artifact with one or more of the transducer elements may comprise performing a scan using the transducer unit to identify the elements which are potentially corrupted by the artifact.

For example, the scan may comprise transmitting an ultrasound pulse into the general area being probed. From this, a simple image may be reconstructed and based on the reconstructed image, a location of a physical occlusion can be determined. For example, a plane wave may be transmitted into the general area being probed. Those transducer elements receiving only a low strength echo may be transducers affected by, e.g. aligned with an artifact.

The artifact may for example include one or more air bubbles trapped e.g. in the gel interfacing between the transducer unit and the body surface or a bone structure obscuring the elements.

If no potential artefacts are found during the artifact detection step, the measured change in the parameter value is considered a genuine change, and not indicative of any obstruction. If an artifact is found, then subsequent measurements are performed using ultrasound data acquired from each of the consecutive areas or portions of transducer elements which are not corrupted by the artifact. The affected transducer elements may not be activated by the controller for generating signals for future measurement, or any collected data from these elements may be discounted.

As briefly mentioned above, the optimization step to minimize a noise component in the physiological parameter to be measured can be performed in variety of ways. At least two key approaches can be identified.

One approach is based on minimizing noise at the level of individual transducer signals, for example by reducing weightings for transducers whose returned signals in the presence of the artefact exhibit a high noise component or low SNR. This assumes that an expected noise component in the parameter measurement is related to noise in the underlying ultrasound transducer signals. Another approach is to minimize noise at the (higher) level of the measured parameter itself, for example by using a model or estimation algorithm for estimating the parameter and/or the error component of it, this for example being based on prior derived or observed patterns in the data, allowing estimation of the expected parameter or noise when different weightings are used.

According to the first approach for instance, the optimization procedure may comprise applying relative higher amplitude weightings to transducer elements for which received ultrasound signals at the element in the presence of the artefact exhibit a relative lower noise, and applying relative lower weightings to transducer elements for which received ultrasound signals exhibit relative higher noise.

By way of example, the controller unit may be adapted to measure the physiological parameter of blood flow through a blood vessel. In this case, the optimization procedure may comprise controlling each transducer element to transmit a Doppler signal and for each transducer element and determining the reception quality of the received Doppler waveform. Weighting coefficients may then be set at a relative high level for elements which receive the reflected Doppler (burst) with a high reception quality (low noise level), and vice versa.

A similar possible method according to this first approach comprises for example comparing ultrasound data received at each transducer element with an average of the ultrasound data received across all of the transducer elements (or at least a subset of them). A deviation from said average for each transducer element may be determined, and an estimated noise component may be assumed to be related to said deviation. In particular, transducer elements for which received ultrasound data or signals exhibits a high deviation from the average may be assigned lower weighting coefficients and vice versa.

For instance, lines that give deviation responses (e.g., due to some blockage, shadow, or poor alignment with the anatomical region of interest) will exhibit a large absolute (squared) difference from the average line. This may be taken to be indicative of a high expected noise component in any parameter measurement derived based on data from that transducer element.

According to the second approach, there still further options.

The optimization procedure may be based on use of an estimation procedure to estimate expected values of the at least one physiological parameter and/or the expected noise component of the physiological parameter.

In particular examples, the estimation procedure may be based on estimating the expected values of the parameter or the noise component when derived using data acquired from different subsets of one or more of the non-associated transducer elements. Hence from this, the noise levels contributed by different subsets of elements to the measured parameter can be determined, and this can inform which elements should be weighted more highly (those with low estimated noise contribution) and which less highly (those with higher estimated noise contribution).

In other examples, the estimation procedure may be based on estimating the expected values of the parameter or the noise component if derived from the non-associated transducer elements being configured with different sets of possible weightings.

The best set of weightings can then be identified as those which produce the lowest estimated noise component in the parameter value. This set of weightings may then be selected as the optimized weighting to apply to the transducer elements.

Estimating the parameter value and/or noise component for the different transducer elements (or subsets thereof) or different weightings, may be based on a model of the parameter behavior, and/or based on prior knowledge of the (behavior/pattern of) the parameter.

According to one set of embodiments for instance, a model may be used which is configured to determine an expected measured value for a given parameter, for instance based on past derived measurements for the parameter (e.g. an averaged parameter measurement). A noise component for each transducer element may then be determined based on a comparison of a derived or estimated parameter measurement calculated using data from the transducer element, with the modeled expected measurement. Transducer elements with a higher deviation from the expected measurement (for instance a higher (squared) absolute difference) may be assigned lower weighting coefficients and vice versa.

According to one or more examples, the estimation procedure (i.e. estimating the noise component contributed by the different transducer elements (or subsets thereof)) is based on determined or pre-determined knowledge of a relative position and/or geometry of an anatomical element to which the physiological parameter to be measured pertains, relative to the ultrasound transducer unit.

Hence estimation may be based on geometrical considerations relating to the anatomical body to which the measured physiological parameter pertains.

For instance, by way of one example, the system may be configured for measuring physiological properties pertaining to the anatomical element of a blood vessel, such as the pulsations of the vessel wall or relative blood flow through the vessel. Preferably, instead of determining these parameters with image processing from an image, as explained above, (for reasons of maximizing signal to noise) it is better in cases of artefacts in the transducer output path, to instead create and receive a pulse perpendicular to the vessel wall (using the non-affected transducers). Parameters pertaining to the vessel may be then directly determined from the ultrasound signal without image reconstruction.

As discussed above, the weighting coefficients of the transducer elements may be adjusted according to the quality of parameter estimation expected to be derivable from their data, i.e. the contribution each is expected to make to the signal-to-noise of the derived parameter measurement. Furthermore, this may in part derive from geometrical factors. For example, in a three-dimensional transducer array transmitting a plane wave toward a vessel, some transducer elements will have output paths which more directly or accurately intercept or bisect the vessel, and measurements obtained from the data of these elements will naturally be of higher quality and contribute to high signal to noise in the parameter measurement. Ideally these should be assigned a higher amplification weighting. By contrast transducer elements poorly aligned with the anatomical element to which the measured parameter pertains will generate noise in the derived parameter measurement. Ideally, these should be obtained a lower amplification weighting.

An estimate of the noise component contributed by different transducer elements may be derived based on a model, for example based on a geometrical model of shape and/or position of the anatomical element/body to which the measured parameter pertains, for instance including its position in relation to the transducer elements of the transducer unit. From this, an estimated signal-to-noise contribution of the data derived from each transducer element may be derived, based for instance upon the respective transducer element's position (e.g. angular position and/or distance) relative to the anatomical element to which the measured parameter pertains.

A location of the anatomical element to which the measured physiological parameter pertains, e.g. a blood vessel, may be derived in some cases using an ultrasound image reconstruction. However, alternatively a geometrical model may be used, for instance modeling the vessel as a simple tube with a certain orientation and depth.

This geometrical model may be associated with a corresponding ultrasound signal model. For example, when analyzing a blood vessel parameter, a model for each transducer element (assuming plane waves) may comprise a pattern consisting of a certain duration of high intensities (corresponding to tissue above the vessel), a certain duration of low intensity (corresponding to the blood vessel) followed by a certain duration of high intensities (corresponding to tissue below vessel).

A tube depth and orientation may then be derived based on analyzing received ultrasound data and identifying this characteristic pattern in the data.

Alternatively, a geometrical location and/or size of the blood vessel may be derived using for instance Color Doppler ultrasound data to identify a blood flow, identify the blood flow area. The blood flow area may be used as a mask to fit a tube as described above which represents the blood vessel.

Once location and optionally dimensions of the anatomical element to which the parameter to be measured has been derived, an estimation may be derived of an expected noise level contributed to the measured parameter by data generated by each of the transducer elements, based for instance on a relative position of each element to the vessel.

For this, a more comprehensive model may be used which defines a relationship between position and/or geometry of the anatomical element to which the physiological parameter being measured pertains and an estimated noise level of a parameter derived from each of a set of transducer elements of a transducer unit. This model may take into account a relative distance and angular position of each transducer element to the anatomical element, based on position and geometry of the element. The model may provide as an output as estimated noise contribution of each transducer element to a parameter measurement.

According to further examples, an estimated noise component of a transducer element may be estimated based on signal properties of the received ultrasound signal such as signal contrast. Here, lower signal contrast may be associated with higher estimated noise contribution to physiological parameter measurements, and so may be assigned lower amplification weightings.

For example, one parameter which may be measured is a continuous estimation of a diameter of a partially clogged blood vessel. A transducer unit's aperture and element delays are set such that a set of sub apertures are created and for each sub-aperture vessel diameter measurements may be performed. For those elements for which derived measurements have a lower noise, based on a measured signal contrast, an underlying model or cross measurement consistency for instance, the element weighting coefficients are adjusted, such that elements producing a higher quality measurements are assigned greater weight than diameter estimates with a lower weight.

In another example, a Doppler image (color Doppler) is created first to determine the location of an anatomical element, e.g. a vessel, based on detected flow through that vessel. Transducer element weightings may be set in accordance with proximity of the element to the vessel, e.g. closer elements assigned a higher weighting.

The prior data may include prior derived parameter measurements for different sets of applied weightings and/or for data of different subsets of one or more transducer elements. The prior data may include or indicate prior trends or patterns in the parameter values over a time series, in examples.

The data can be used for different purposes. The prior data can be used as a basis for deriving the estimated parameter values or noise components for different subsets of one or more transducer elements. For example, an average past value can be derived for a particular element or subset based on prior values, and used to inform an estimated value of the parameter.

Additionally or alternatively, the data can be used to derive an estimate of a noise component in the data based on independently deriving estimated values of the parameter, and comparing these with past data or trends in the data.

Accordingly, the estimation procedure may be based on comparing derived estimated values of the at least one parameter using different sets of weightings or using different subsets of one or more transducer elements with prior data in said stored dataset, to thereby derive an estimation of a noise component of said values, based on identified disparities.

According to any embodiments, the deriving of the further measurements may comprise compounding data acquired from each of one or more consecutive sets of the non-affected transducer elements.

Optionally, the compounding may comprise averaging, e.g. a weighted average. The consecutive sets refers for example to each interrupted chain or block of elements, e.g. on either side of the artifact or obstruction.

According to one set of examples, separate consecutive sets of non-affected transducer elements may be optimized separately (sequentially). By way of one example, if elements 51-89 of an array of 128 elements are blocked by an air bubble for instance, a parameter measurement may first be performed with only elements 1-50, after which the weightings for these elements are optimized in accordance with any of the example procedures described above. Subsequently, the same is done for elements 90-128. This process may be completed at high speed, so as to not affect the monitoring reliability. After the optimized weighting coefficients have been configured, monitoring of the physiological parameter of interest may continue. Measurements obtained from different element areas may be combined (e.g. weighted according to the number of elements in each area and then averaged). The result may be output on a visual display in some examples.

The discussed herein innovative solution enables an application of the ultrasound array, which is still mostly used in ultrasound diagnostic imaging, in a monitoring domain, wherein tracking a change in physiological parameters with time is used by a clinician in assessing real time status of a patient. The optimization procedure of the at least one physiological parameter measure performed by the processor enables an automated control of the ultrasound transducer unit for the most optimal physiological parameter acquisition will reduced interference from the user. This opens up a wider acceptance of the ultrasound technology in a non-invasive monitoring area, which is inherently supported by low skilled in ultrasound imaging users.

In the case that multiple physiological parameters are to be measured from a single ultrasound signal input, the parameter optimization procedure is preferably configured to take account of both parameters. In some examples, the relative clinical importance/weight of each parameter might be configured (for instance based on a user input, from a clinician), or a priority order may be set for the parameters. The degree to which the transducer element weightings are optimized for each of the parameters (i.e. improving the quality of one parameter at the expense of the quality of another) may be configured. It may be configurable via a user input for example, or the relative priority may be pre-set in advance.

Figure 4:
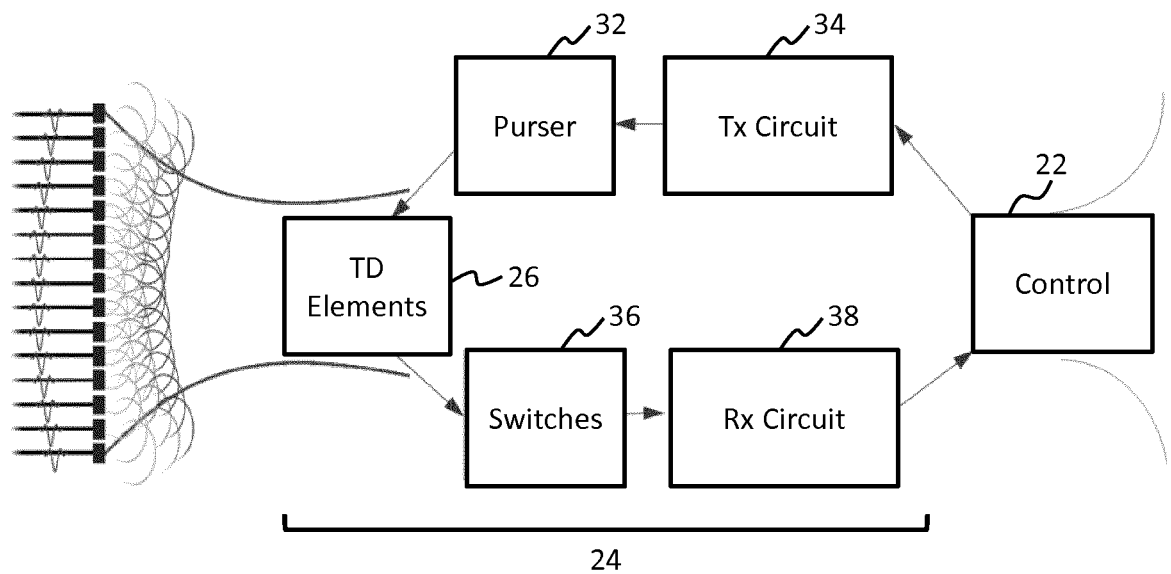
FIG. 4 shows a block diagram of components of an example ultrasound transducer unit.

FIG. 4 schematically depicts the components of the example system of FIG. 3 in more detail, including various components of the transducer unit 24. The transducer unit comprises transducer elements 26. These are driven by transmit electronics, comprising a transmit circuitry block ("Tx Circuit") 34 and a Pulser block 32. The transducer unit further comprises receive electronics, comprising high voltage switches 36 for controlling switching of the transducer element 26 and receive circuitry ("Rx Circuit") 38. Both the receive and transmit electronics are controlled via the operably coupled controller 22, which also processes the ultrasound data to construct images.

The transmit 34 and receive 38 electronics of FIG. 4 set weighting coefficients for application to both transmitted and received signals in accordance with a synchronized control input received from the controller 22. Weighting coefficients are set for each transducer element or channel based on the control input of the controller.

The transmit electronics for example configures the transmit weighting coefficients and outputs them to the pulser 32 for generating the weighted signal pulses for transmission to the transducer elements 26. The transmit electronics also configures the pulse delay times for the transducer elements, for configuring beamforming.

The receive electronics block 38 configures further receive weighting coefficients and applies these to received ultrasound signals before outputting the resulting data to the controller unit 22 for estimating the one or more physiological parameters.

A further aspect of the invention provides a body mountable ultrasound unit comprising an ultrasound transducer unit and a coupled controller.

Figure 5:
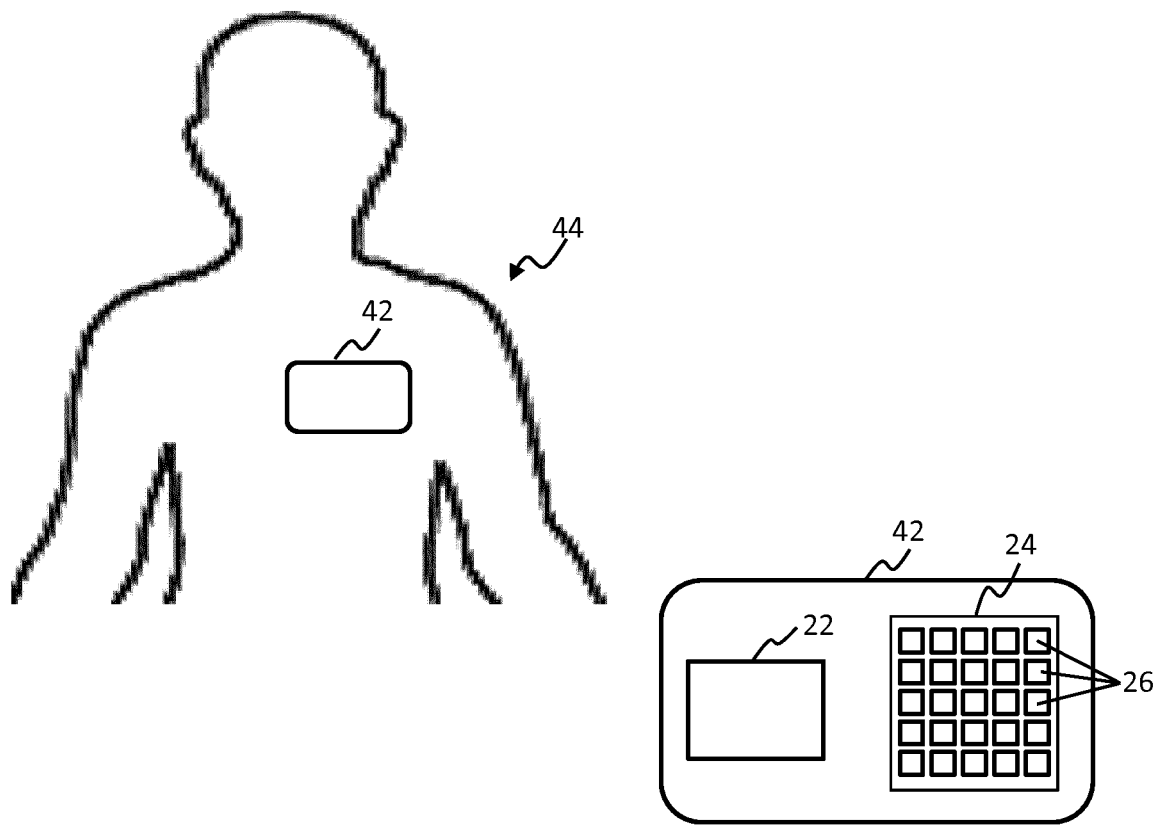
FIG. 5 shows an example body-mountable ultrasound unit according to an embodiment.

An example is shown schematically in FIG. 5. In this example the body mountable ultrasound unit is in the form of a body-mountable patch unit 42 for removably coupling to the skin of a subject 44. FIG. 5 schematically shows the components of the ultrasound unit 42 (patch in this example) in more detail. The ultrasound unit comprises a controller unit 22 operably coupled to an ultrasound transducer unit 24 comprising a plurality of ultrasound transducer elements 26, in this example configured as an array of transducer elements. The elements may take other configurations, for example having a linear or two dimensional arrangement.

The transducer elements 26 of the transducer unit 24 are arranged for acoustically coupling with the skin of the subject 44 when the patch is in a mounted position on the body of the subject. For example the transducer elements may have acoustic output/input surfaces or parts which are acoustically coupled with a body-contact surface of the patch, e.g. exposed at a body-contact surface of the patch. The body-contact surface is the surface arranged for contacting the body when the patch is mounted to the body. The body contact surface may be partially or fully covered by an adhesive layer for adhering the patch to the skin of the patient. The adhesive layer may extend around the transducer array to avoid interfering with the acoustic coupling with the skin.

Although the body mountable unit is in the form of a body-mountable patch in the example of FIG. 5, this is by way of one example only. In other examples, the body mountable unit may be any unit configured for removably mounting or attaching to a part of the body, for instance either a surface of the body or a limb or structure of the body. For example, the unit may be configured for mounting to any of: the wrist, chest, leg, head, arm, ear or any other part of the body. The unit may be a wearable unit, e.g. a wrist wearable unit.

A further aspect of the invention provides a method of configuring an ultrasound transducer unit, the unit being adapted to acquire ultrasound data for deriving a measure of one or more physiological parameters, and having a configurable set of amplification weighting coefficients applied to transmitted and received ultrasound signals of each of a plurality of transducer elements of the transducer unit.

Figure 6:
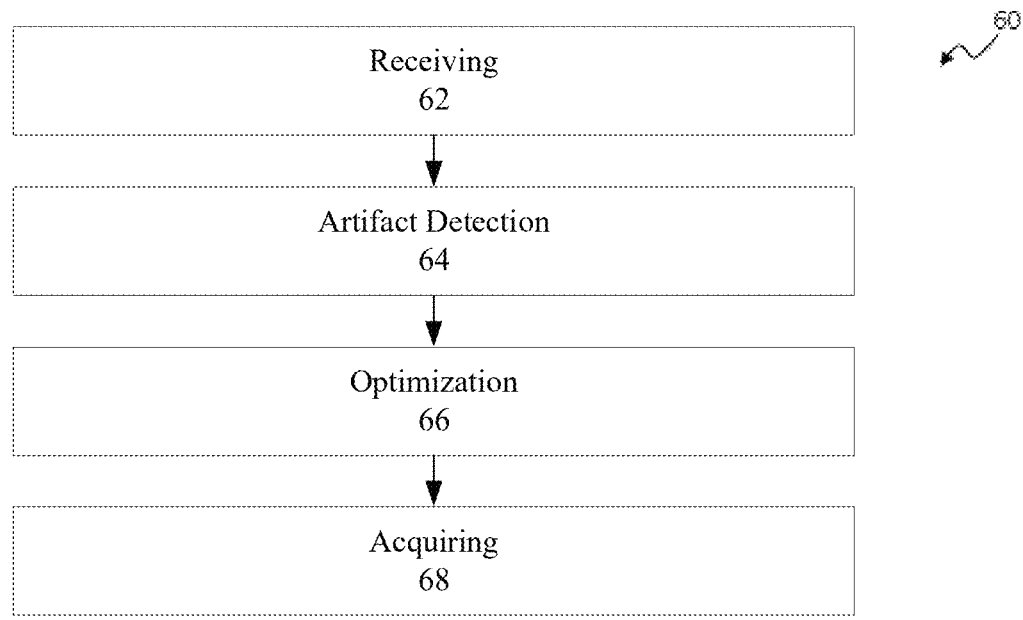
FIG. 6 shows an example method according to an embodiment.

An example method 60 according to one or more embodiments is shown in block diagram form in FIG. 6.

The method first comprises receiving 62 ultrasound data from the transducer unit. Following this artifact detection 64 is performed to detect the presence of any artefacts in the received data. This step further includes and associating any detected artefacts with the signal data of one or more of the transducer elements.

Following artifact detection, the method 60 comprises performing an optimization procedure 66 for the at least one physiological parameter measurement, comprising adjusting the amplification weighting coefficients of the non-associated transducer elements to minimize an expected noise component in the physiological parameter measurement when derived from data of the non-associated transducers only.

Subsequent to the optimization procedure, the method further comprises acquiring 68 further ultrasound data using only the non-affected transducer elements, the elements being configured with the optimized weighting coefficients, and deriving further measurements of the at least one physiological parameter based on the acquired data.

The procedures performed for these steps should be understood in light of the explanations provided for the equivalent processes in the apparatus aspect of this invention, described in detail above. All options and embodiments described and explained in relation to the ultrasound controller unit 22 aspect of the invention may be applied equally to this method aspect of the invention to provide an equivalent set of method embodiments according to the invention.

As noted above, the ultrasound controller unit 22 of the invention may be provided as part of a broader ultrasound system, for configuring ultrasound transducer elements of the system.

Figure 7:
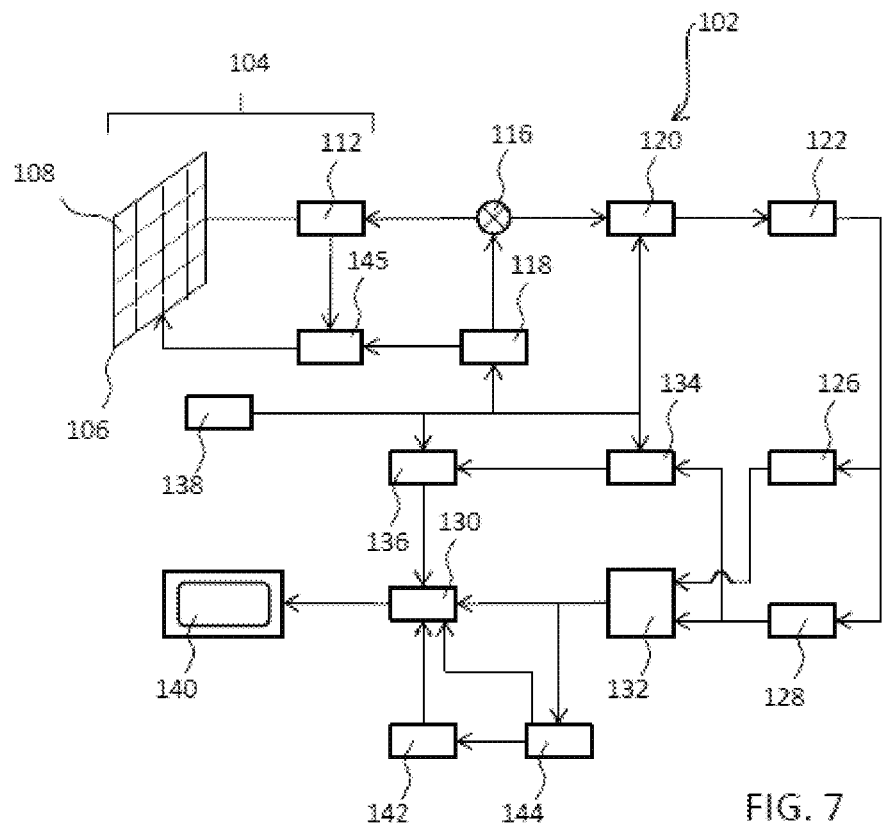
FIG. 7 shows an example ultrasound system.

By way of further, more detailed explanation, the general operation of an exemplary ultrasound system will now be described, with reference to FIG. 7, and with emphasis on the signal processing function of the system since this invention relates to the processing of the signals measured by the transducer array.

The system comprises an array transducer probe 104 which has a transducer array 106 for transmitting ultrasound waves and receiving echo information. The transducer array 6 may comprise CMUT transducers; piezoelectric transducers, formed of materials such as PZT or PVDF; or any other suitable transducer technology. In this example, the transducer array 106 is a two-dimensional array of transducers 108 capable of scanning either a 2D plane or a three dimensional volume of a region of interest. In another example, the transducer array may be a 1D array.

The transducer array 106 is coupled to a microbeamformer 112 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is in general entirely optional. Further, the system includes a transmit/receive (T/R) switch 116, which the microbeamformer 112 can be coupled to and which switches the array between transmission and reception modes, and protects the main beamformer 120 from high energy transmit signals in the case where a microbeamformer is not used and the transducer array is operated directly by the main system beamformer. The transmission of ultrasound beams from the transducer array 106 is directed by a transducer controller 118 coupled to the microbeamformer by the T/R switch 116 and a main transmission beamformer (not shown), which can receive input from the user's operation of the user interface or control panel 138. The controller 118 can include transmission circuitry arranged to drive the transducer elements of the array 106 (either directly or via a microbeamformer) during the transmission mode.

The function of the control panel 138 in this example system may be facilitated by an ultrasound controller unit according to an embodiment of the invention.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 118 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 118 can be coupled to control a DC bias control 145 for the transducer array. The DC bias control 145 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 112 and are then passed to a main receive beamformer 120 where the partially beamformed signals from individual patches of transducers are combined into a fully beamformed signal, referred to as radio frequency (RF) data. The beamforming performed at each stage may be carried out as described above, or may include additional functions. For example, the main beamformer 120 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 122. The signal processor 122 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 7 only the receiver beamformers 112, 120 are shown, for simplicity. In the complete system, there will also be a transmission chain with a transmission micro beamformer, and a main transmission beamformer.

The function of the micro beamformer 112 is to provide an initial combination of signals in order to decrease the number of analog signal paths. This is typically performed in the analog domain.

The final beamforming is done in the main beamformer 120 and is typically after digitization.

The transmission and reception channels use the same transducer array 106 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 126 and a Doppler processor 128. The B mode processor 126 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 132 and a multi-planar reformatter 144. The scan converter 132 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 140. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.).

The 2D or 3D images are coupled from the scan converter 132, multi-planar reformatter 144, and volume renderer 142 to an image processor 130 for further enhancement, buffering and temporary storage for optional display on an image display 140. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 128 and tissue structure information produced by the B mode processor 126 are coupled to a quantification processor 134. The quantification processor produces measures of different flow conditions such as the volume rate of blood flow in addition to structural measurements such as the sizes of organs and gestational age. The quantification processor may receive input from the user control panel 138, such as the point in the anatomy of an image where a measurement is to be made. More preferably, for embodiments of this invention, the controller unit 22 of embodiments of the invention may comprise the quantification processor for deriving the estimates of the physiological parameter of interest.

Output data from the quantification processor is coupled to a graphics processor 136 for the reproduction of measurement graphics and values with the image on the display 140, and for audio output from the display device 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 138, such as patient name. The user interface is also coupled to the transmit controller 18 to control the generation of ultrasound signals from the transducer array 6 and hence the images produced by the transducer array and the ultrasound system. The transmit control function of the controller 118 is only one of the functions performed. The controller 118 also takes account of the mode of operation (given by the user) and the corresponding required transmitter configuration and bandpass configuration in the receiver analog to digital converter. The controller 118 can be a state machine with fixed states.

The user interface is also coupled to the multi-planar reformatter 144 for selection and control of the planes of multiple multi-planar reformatted (MPR) images which may be used to perform quantified measures in the image field of the MPR images.

Advantageously, the B mode processor 126, Doppler processor 128, scan converter 132, multi-planar reformatter 144, volume renderer 142, image processor 130, quantification processor 134, and/or graphics processor 136 may be comprised by the ultrasound controller unit 22 in one or more embodiments of the present invention to facilitate image reconstruction and estimation of the physiological parameter of interest.

As discussed above, embodiments make use of a controller (unit). The controller (unit) can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An ultrasound controller unit for receiving and processing ultrasound data to derive a measure of at least one physiological parameter, the ultrasound controller unit being operably couplable with an ultrasound transducer unit, for controlling the ultrasound transducer unit to acquire the ultrasound data, and for controlling a set of amplification weighting coefficients applied to transmitted and received ultrasound signals of each of a plurality of transducer elements of the ultrasound transducer unit, including at least one weighting coefficient of the set of amplification weighting coefficients for each of the plurality of transducer elements, the ultrasound controller unit being adapted to:

receive the acquired ultrasound data from the ultrasound transducer unit, perform artifact detection to detect presence of any artifact in the received ultrasound data, and associate any detected artifact with signal data of at least one of the plurality of transducer elements, perform an optimization procedure for the measure of the at least one physiological parameter to be derived, comprising adjusting the weighting coefficients of the set of amplification weighting coefficients of non-associated transducer elements of the plurality of transducer elements to minimize an expected noise component in the measure of the at least one physiological parameter to be derived when derived from ultrasound data of only the non-associated transducers, and control the ultrasound transducer unit to transmit ultrasound signals and receive ultrasound echoes using only the non-associated transducer elements of the plurality of transducer elements to acquire further ultrasound data, the non-associated transducer elements of the plurality of transducer elements being configured with the adjusted weighting coefficients of the set of amplification weighting coefficients, and derive the measure of the at least one physiological parameter based on said further acquired ultrasound data.

2. The ultrasound controller unit as claimed in claim 1, wherein the expected noise component is based on detected signal noise in the ultrasound signals received at the plurality of transducer elements in the presence of the detected artifact.

3. The ultrasound controller unit as claimed in claim 2, wherein the optimization procedure comprises applying relative higher weightings for the weighting coefficients of the set of amplification weighting coefficients to transducer elements of the plurality of transducer elements for which received ultrasound signals in the presence of the detected artifact exhibit a relative lower noise, and applying relative lower weightings for the weighting coefficients of the set of amplification weighting coefficients to transducer elements of the plurality of transducer elements for which received ultrasound signals exhibit relative higher noise.

4. The ultrasound controller unit as claimed in claim 1, wherein the expected noise component is derived based on use of an estimation procedure for estimating expected values of the at least one physiological parameter and/or the expected noise component of the at least one physiological parameter.

5. The ultrasound controller unit as claimed in claim 4, wherein the estimation procedure is based on estimating said expected values of the at least one physiological parameter or the expected noise component when derived using data of different subsets of at least one of the non-associated transducer elements of the plurality of transducer elements, and/or if derived from the non-associated transducer elements of the plurality of transducer elements being configured with different sets of possible weightings for the weighting coefficients of the set of amplification weighting coefficients.

6. The ultrasound controller unit as claimed in claim 4, wherein the estimation procedure is based on a determined or known relative position of an anatomical element to which the at least one physiological parameter to be measured pertains, relative to the ultrasound transducer unit.

7. The ultrasound controller unit as claimed in claim 6, wherein the relative position of said anatomical element is determined based on an analysis of patterns in the further acquired ultrasound data, and performed without generation of an ultrasound image from the further acquired ultrasound data.

8. The ultrasound controller unit as claimed in claim 4, wherein the estimation procedure is based on use of a stored dataset of prior data relating to previously derived values of the at least one physiological parameter.

9. The ultrasound controller unit as claimed in claim 8, wherein the estimation procedure is based on comparing derived estimated values of the at least one physiological parameter using different sets of weightings for the weighting coefficients of the set of amplification weighting coefficients or using different subsets of at least one of the plurality of transducer elements with the prior data in said stored dataset, to thereby derive an estimation of an expected noise component of said values, based on identified disparities.

10. The ultrasound controller unit as claimed in claim 8, wherein the prior data includes prior derived parameter measurements for different sets of applied weightings for weighting coefficients of the set of amplification weighting coefficients and/or for data of different subsets of at least one of the plurality of transducer elements.

11. The ultrasound controller unit as claimed in claim 1, wherein the deriving the measure of the at least one physiological parameter using the optimized weighting coefficients of the set of amplification weighting coefficients comprises directing at least one ultrasound plane wave toward an anatomical element to which the at least one physiological parameter pertains.

12. The ultrasound controller unit as claimed in claim 1, wherein the deriving the measure of the at least one physiological parameter using the optimized weighting coefficients of the set of amplification weighting coefficients is based on analysis of the ultrasound data without generating an ultrasound image.

13. The ultrasound controller unit as claimed in claim 1, wherein the deriving of the measure of the at least one physiological parameter comprises compounding data acquired from each of at least one consecutive set of the non-associated transducer elements of the plurality of transducer elements.

14. The ultrasound controller unit as claimed in claim 1, wherein the artifact detection comprises monitoring received ultrasound data and/or at least one derived physiological parameter for a characteristic deviation in the received ultrasound data or the at least one physiological parameter from previously acquired values.

15. A body-mountable ultrasound unit, comprising:
an ultrasound transducer unit comprising a plurality of transducer elements and having a set of configurable amplification weighting coefficients for applying to transmitted and received ultrasound signals of each of the plurality of transducer elements, including at least one configurable weighting coefficient of the set of configurable amplification weighting coefficients for each transducer element of the plurality of transducer elements; and
an ultrasound controller unit as claimed in claim 1, operably coupled with the ultrasound transducer unit for controlling the ultrasound transducer unit.

16. The body-mountable ultrasound unit as claimed in claim 15, wherein the body mountable ultrasound unit is in a form of a body-mountable patch.

17. A method of configuring an ultrasound transducer unit,
the ultrasound transducer unit being adapted to acquire ultrasound data for deriving a measure of at least one physiological parameter, and having a configurable set of amplification weighting coefficients applied to transmitted and received ultrasound signals of a plurality of transducer elements of the ultrasound transducer unit, including at least one weighting coefficient for each transducer element of the plurality of transducer elements,
the method comprising:
receiving the acquired ultrasound data from the ultrasound transducer unit;
performing artifact detection to detect presence of any artifact in the received ultrasound data, and associating any detected artifact with signal data of at least one of the plurality of transducer elements,
performing an optimization procedure for the measure of the at least one physiological parameter, comprising adjusting the weighting coefficients of the set of amplification weighting coefficients of non-associated transducer elements of the plurality of transducer elements to minimize an expected noise component in the measure of the at least one physiological parameter when derived from data of only the non-associated transducer elements of the plurality of transducer elements, and
controlling the ultrasound transducer unit to transmit ultrasound signals and receive ultrasound echoes using only the non-associated transducer elements of the plurality of transducer elements to acquire further ultrasound data, the plurality of transducer elements of the plurality of transducer elements being configured with the adjusted weighting coefficients of the set of amplification weighting coefficients, and
deriving a further measure of the at least one physiological parameter based on said further acquired ultrasound data.

* * * * *